US009530198B2

(12) United States Patent
Temmei et al.

(10) Patent No.: US 9,530,198 B2
(45) **Date of Patent: *Dec. 27, 2016**

(54) METHOD FOR CONTROLLING X-RAY IMAGE DIAGNOSIS APPARATUS AND X-RAY GENERATION DEVICE

(71) Applicants: Konosuke Temmei, Tokyo (JP); Yuji Sakai, Tokyo (JP); Tadashi Nakamura, Tokyo (JP)

(72) Inventors: Konosuke Temmei, Tokyo (JP); Yuji Sakai, Tokyo (JP); Tadashi Nakamura, Tokyo (JP)

(73) Assignee: HITACHI, LTD., Tokyo (JP)

( * ) Notice: Subject to any disclaimer, the term of this patent is extended or adjusted under 35 U.S.C. 154(b) by 198 days.

This patent is subject to a terminal disclaimer.

(21) Appl. No.: 14/389,779

(22) PCT Filed: Mar. 18, 2013

(86) PCT No.: PCT/JP2013/057582

§ 371 (c)(1),
(2) Date: Oct. 1, 2014

(87) PCT Pub. No.: WO2013/150884

PCT Pub. Date: Oct. 10, 2013

(65) Prior Publication Data

US 2015/0071406 A1 Mar. 12, 2015

(30) Foreign Application Priority Data

Apr. 2, 2012 (JP) ................................. 2012-084111

(51) Int. Cl.
*G06T 7/00* (2006.01)
*A61B 6/00* (2006.01)
(Continued)

(52) U.S. Cl.
CPC ............. *G06T 7/0004* (2013.01); *A61B 6/469* (2013.01); *G06K 9/38* (2013.01); *G06K 9/4642* (2013.01);
(Continued)

(58) Field of Classification Search
CPC ........... A61B 6/469; A61B 6/505; A61B 6/52; A61B 6/54; G06K 9/4642; G06K 9/38; G06K 2209/055; G06T 7/004; G06T 7/0081; G06T 7/403; G06T 2207/20144; G06T 2207/30008; G06T 2207/20021; G06T 2207/10121
See application file for complete search history.

(56) References Cited

U.S. PATENT DOCUMENTS 6,377,656 B1 4/2002 Ueki et al.
2004/0066897 A1 4/2004 Takahashi et al.
2014/0140606 A1* 5/2014 Temmei ................. A61B 6/542 382/132

FOREIGN PATENT DOCUMENTS

CN 1255279 A 5/2000
CN 1498093 A 5/2004
(Continued)

OTHER PUBLICATIONS

International Search Report issued in corresponding application No. PCT/JP2013/057582 mailed on Apr. 13, 2013.
(Continued)

*Primary Examiner* — Courtney Thomas
(74) *Attorney, Agent, or Firm* — Brundidge & Stanger, P.C.

(57) ABSTRACT

To provide a method for controlling an X-ray image diagnostic apparatus and an X-ray generation device equipped with an ABS system tracking movement of an object position without an operator performing setting operation for a region of interest (ROI), the determination condition storage
(Continued)

unit (6*i*) storing ROI position determination conditions in which image statistical information is used for defining conditions to determine a position of an ROI in an X-ray image out of plural blocks generated by dividing the X-ray image into plural regions, the first block statistical information calculation unit (6*f*) calculating the image statistical information for each of plural blocks, and the region-of-interest position selection unit (6*g*) selecting a block that serves as an ROI from among plural blocks using the ROI position determination conditions and the image statistical information of each block are provided. A feedback value to be used in controlling the brightness value of the ROI is calculated based on the brightness value of the ROI, and irradiation conditions are determined so that the feedback value reaches a target brightness value.

14 Claims, 11 Drawing Sheets

(51) Int. Cl.

| | |
|---|---|
| ***G06K 9/46*** | (2006.01) |
| ***G06K 9/38*** | (2006.01) |
| ***G06T 7/40*** | (2006.01) |

(52) U.S. Cl.

CPC ............. *G06T 7/0081* (2013.01); *G06T 7/403* (2013.01); *A61B 6/505* (2013.01); *A61B 6/52* (2013.01); *A61B 6/54* (2013.01); *G06K 2209/055* (2013.01); *G06T 2207/10121* (2013.01); *G06T 2207/20021* (2013.01); *G06T 2207/20144* (2013.01); *G06T 2207/30008* (2013.01)

(56) References Cited

FOREIGN PATENT DOCUMENTS

| | | | |
|---|---|---|---|
| DE | 60228555 | | 10/2008 |
| EP | 1374774 | A1 | 1/2004 |
| JP | 64-017631 | A | 1/1989 |
| JP | 9-055298 | A | 2/1997 |
| JP | 10-308899 | A | 11/1998 |
| JP | 2001-340321 | A | 12/2001 |
| JP | 2002-058665 | A | 2/2002 |
| JP | 2002-344807 | A | 11/2002 |
| WO | 98/52388 | A1 | 11/1998 |
| WO | 02/078546 | A1 | 10/2002 |

OTHER PUBLICATIONS

International Publication issued in corresponding application No. PCT/JP2013/057582 on Oct. 10, 2013.

* cited by examiner

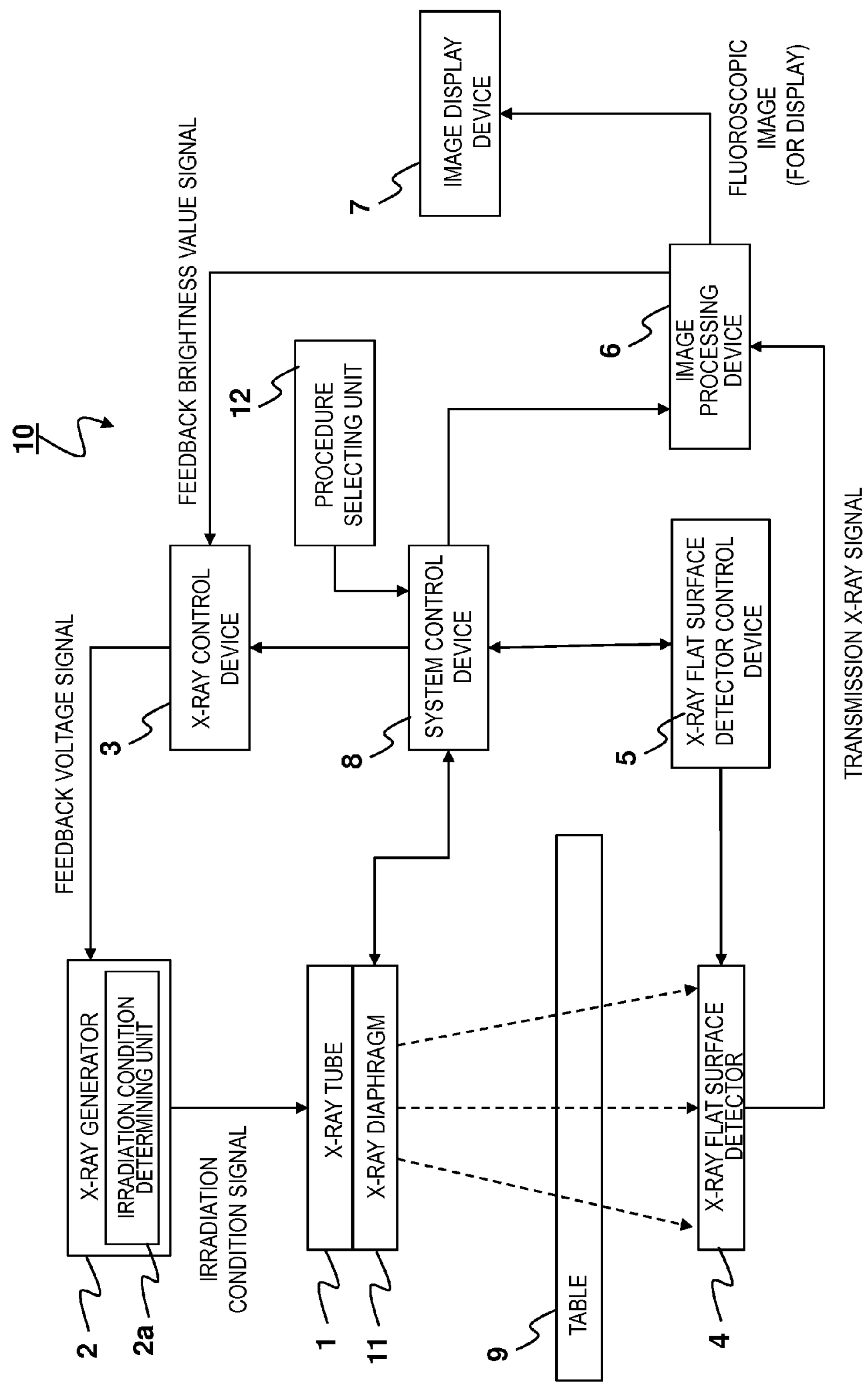
FIG.1
10
2
2a
X-RAY GENERATOR
IRRADIATION CONDITION DETERMINING UNIT
IRRADIATION CONDITION SIGNAL
FEEDBACK VOLTAGE SIGNAL
3
X-RAY CONTROL DEVICE
FEEDBACK BRIGHTNESS VALUE SIGNAL
1
11
X-RAY TUBE
X-RAY DIAPHRAGM
8
SYSTEM CONTROL DEVICE
12
PROCEDURE SELECTING UNIT
7
IMAGE DISPLAY DEVICE
9
TABLE
6
IMAGE PROCESSING DEVICE
FLUOROSCOPIC IMAGE (FOR DISPLAY)
5
X-RAY FLAT SURFACE DETECTOR CONTROL DEVICE
4
X-RAY FLAT SURFACE DETECTOR
TRANSMISSION X-RAY SIGNAL

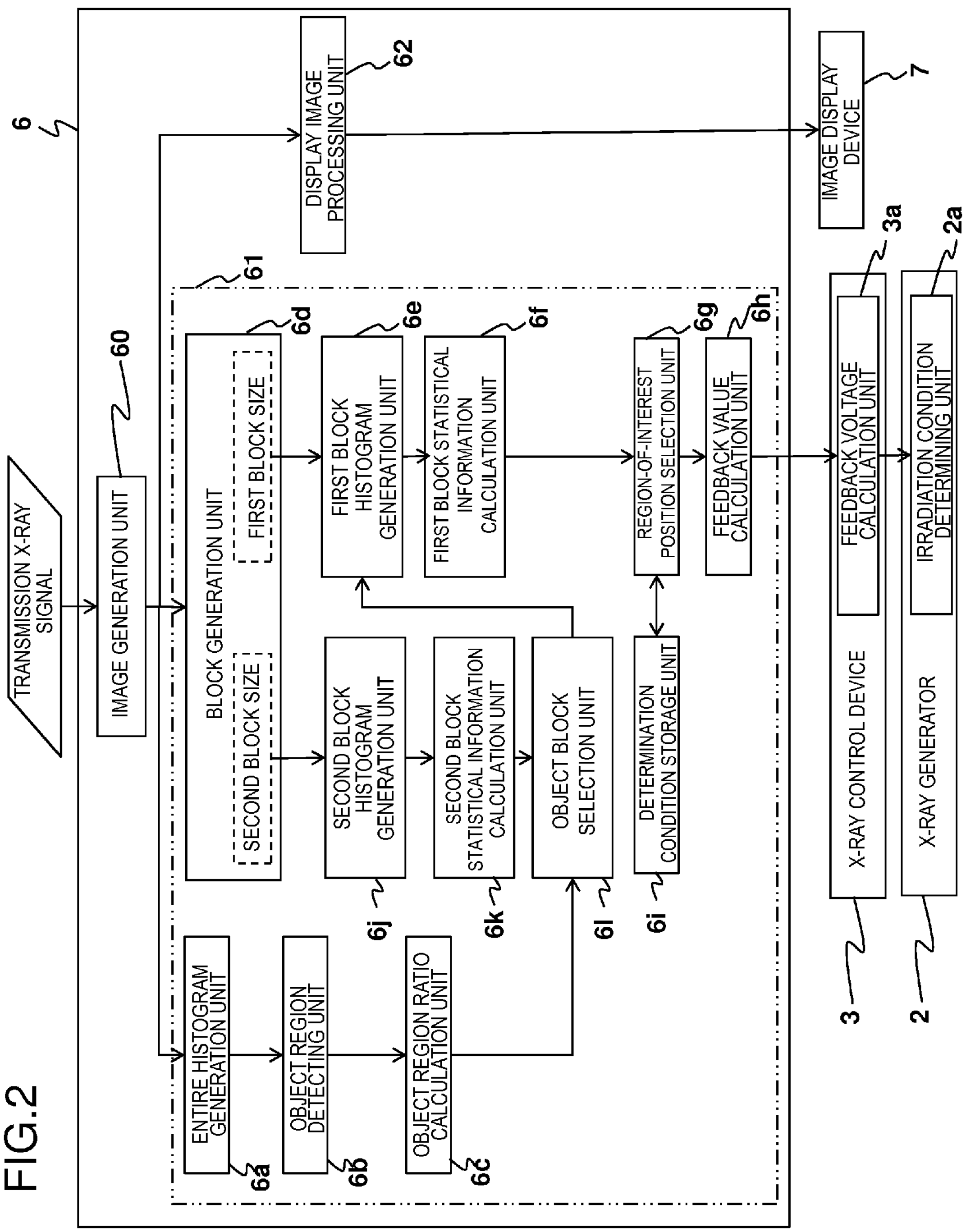
FIG.2
TRANSMISSION X-RAY SIGNAL
IMAGE GENERATION UNIT
BLOCK GENERATION UNIT
FIRST BLOCK SIZE
SECOND BLOCK SIZE
FIRST BLOCK HISTOGRAM GENERATION UNIT
FIRST BLOCK STATISTICAL INFORMATION CALCULATION UNIT
REGION-OF-INTEREST POSITION SELECTION UNIT
FEEDBACK VALUE CALCULATION UNIT
SECOND BLOCK HISTOGRAM GENERATION UNIT
SECOND BLOCK STATISTICAL INFORMATION CALCULATION UNIT
OBJECT BLOCK SELECTION UNIT
DETERMINATION CONDITION STORAGE UNIT
ENTIRE HISTOGRAM GENERATION UNIT
OBJECT REGION DETECTING UNIT
OBJECT REGION RATIO CALCULATION UNIT
DISPLAY IMAGE PROCESSING UNIT
IMAGE DISPLAY DEVICE
FEEDBACK VOLTAGE CALCULATION UNIT
X-RAY CONTROL DEVICE
IRRADIATION CONDITION DETERMINING UNIT
X-RAY GENERATOR
6
60
61
62
6a
6b
6c
6d
6e
6f
6g
6h
6i
6j
6k
6l
7
3
3a
2
2a

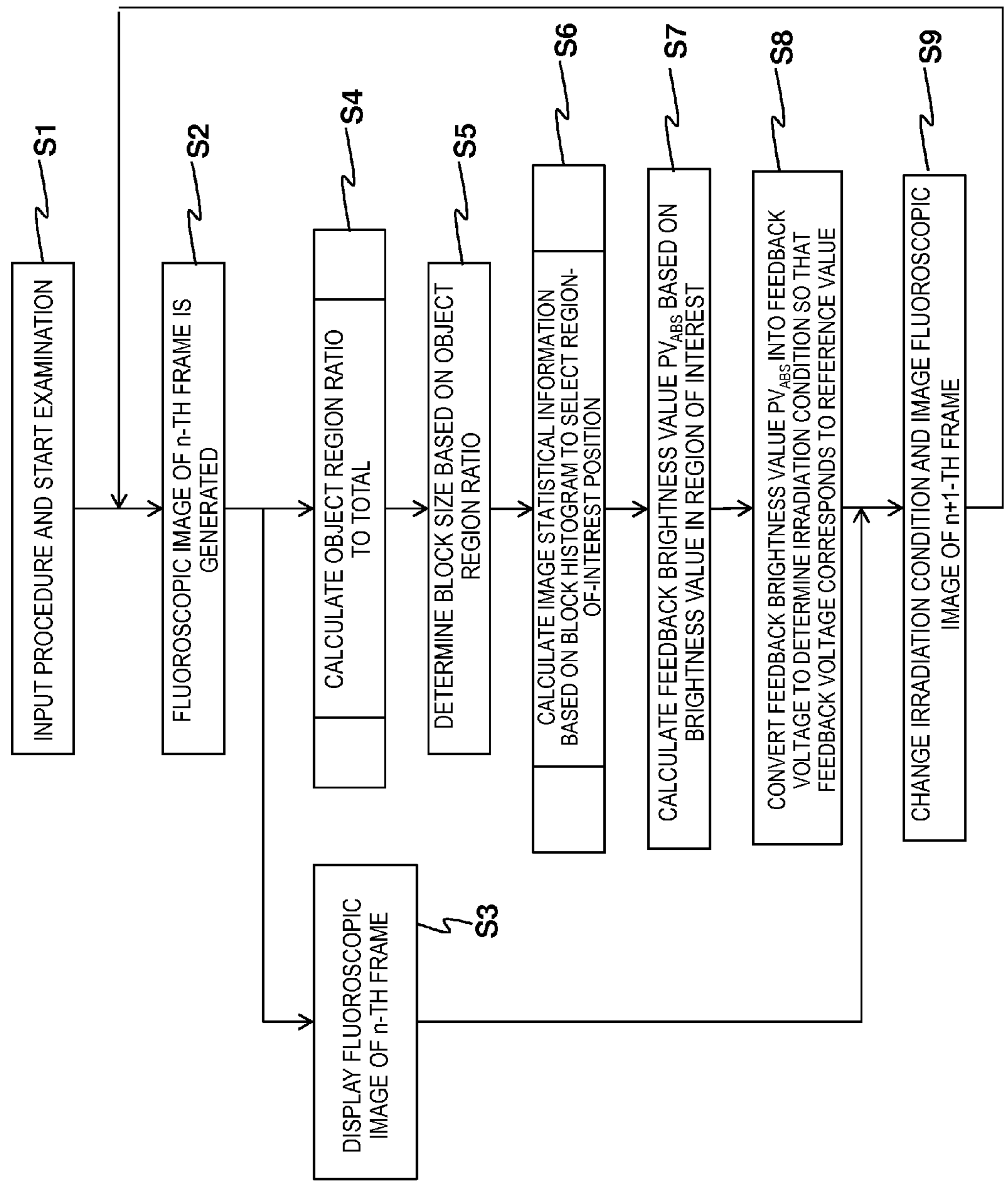
FIG.3
S1
INPUT PROCEDURE AND START EXAMINATION
S2
FLUOROSCOPIC IMAGE OF n-TH FRAME IS GENERATED
S3
DISPLAY FLUOROSCOPIC IMAGE OF n-TH FRAME
S4
CALCULATE OBJECT REGION RATIO TO TOTAL
S5
DETERMINE BLOCK SIZE BASED ON OBJECT REGION RATIO
S6
CALCULATE IMAGE STATISTICAL INFORMATION BASED ON BLOCK HISTOGRAM TO SELECT REGION-OF-INTEREST POSITION
S7
CALCULATE FEEDBACK BRIGHTNESS VALUE $PV_{ABS}$ BASED ON BRIGHTNESS VALUE IN REGION OF INTEREST
S8
CONVERT FEEDBACK BRIGHTNESS VALUE $PV_{ABS}$ INTO FEEDBACK VOLTAGE TO DETERMINE IRRADIATION CONDITION SO THAT FEEDBACK VOLTAGE CORRESPONDS TO REFERENCE VALUE
S9
CHANGE IRRADIATION CONDITION AND IMAGE FLUOROSCOPIC IMAGE OF n+1-TH FRAME

FIG.5

| PROCEDURE | REGION-OF-INTEREST POSITION DETERMINATION CONDITION |
| --- | --- |
| PROCEDURE 1 (ORTHOPEDICS /ARM) | CONDITION 1: BLOCK WHERE NUMBER OF HISTOGRAM PEAK IS ONE |
| | CONDITION 2: BLOCK WHERE AVERAGE BRIGHTNESS VALUE IN BLOCK IS SMALLEST AMONG BLOCKS SATISFYING CONDITION 1 |
| PROCEDURE 2 | CONDITION 1': BLOCK WHERE NUMBER OF HISTOGRAM PEAK IS ONE |
| | CONDITION 2': BLOCK WHERE DISPERSION VALUE OF BRIGHTNESS VALUE IN BLOCK IS SMALLEST AMONG BLOCKS SATISFYING CONDITION 1' |
| PROCEDURE 3 | • • • • • |

FIG.6
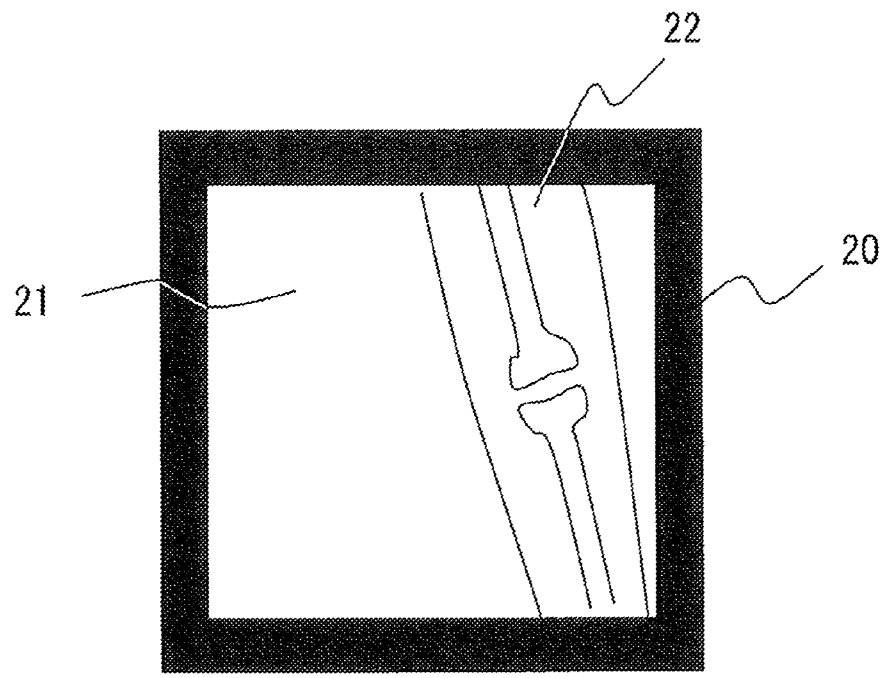
(a)
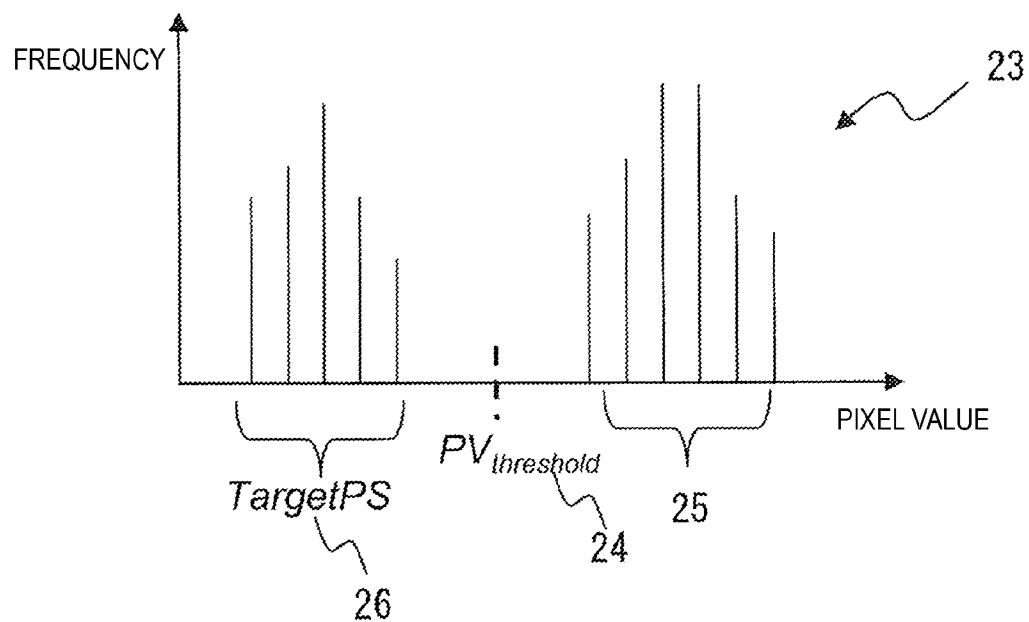
(b)

REVISED VERSION
SECOND BLOCK (b×b)
20
31 (G1 BLOCK)
(a)
FIRST BLOCK (c×c)
32
33 (G2BLOCK)
(b)

REVISED VERSION

FIG.9

| $PV_{ABS}$ | | FEEDBACK VOLTAGE | | X-RAY CONDITION |
|---|---|---|---|---|
| $X_1$ | → | $Y_1$ [V] | → | CHANGE FROM ($mA_1$, $kV_1$) TO ($mA_2$, $kV_2$) |
| $X_2$ | → | $Y_2$ [V] | → | KEEP ($mA_2$, $kV_2$) AS IS |

| PROCEDURE | METAL THRESHOLD VALUE |
| --- | --- |
| PROCEDURE 1 | PV1 |
| PROCEDURE 2 | PV2 |
| PROCEDURE 3 | PV3 |

METHOD FOR CONTROLLING X-RAY IMAGE DIAGNOSIS APPARATUS AND X-RAY GENERATION DEVICE

TECHNICAL FIELD

The present invention relates to a method for controlling an X-ray image diagnosis apparatus and X-ray generation device, in particular to brightness control of an X-ray image.

BACKGROUND ART

Some X-ray image diagnosis apparatuses have the Automatic Brightness Control System (hereinafter, abbreviated as "ABS") that automatically controls a tube voltage so that brightness of a fluoroscopic image is always constant even if an object thickness is changed. As an example of the control method, there is a method where a region of interest is set for an image region output from an X-ray detector; an average brightness value in the region of interest is used as a feedback signal; and a tube voltage is automatically controlled so that a feedback signal value nears a target brightness value set in advance. Then, when the feedback signal is lower than the target brightness value, X-ray output increases by the tube voltage working in a rising direction, and the brightness of the next fluoroscopic image is controlled so that it is brighter than that before rising.

Patent Literature 1 discloses a fluoroscopic imaging apparatus that can set a region of interest with a pointing device such as a mouse during X-ray fluoroscopic imaging and performs feedback for ABS using image data in the region of interest as an example of the ABS control.

CITATION LIST

Patent Literature

PTL 1: Japanese Unexamined Patent Application Publication No. 2005-522237

SUMMARY OF INVENTION

Technical Problem

However, in PTL 1, if an object position is moved by movement of an object, an X-ray tube, etc., and an interested site is out of a region of interest, an operator must re-set and update a position and a size of the region of interest as needed, which results in reducing examination efficiency.

The present invention was made in light of the above problem, and the purpose is to provide the ABS system that tracks movement of an object position without performing setting operation for a region of interest by an operator.

Solution to Problem

In order to solve the above problem, the present invention is characterized by that an X-ray image of an object is divided into plural regions to generate plural blocks, a histogram showing distribution of brightness values for the respective plural blocks is generated, image statistical information to be used for determining a region of interest is calculated based on the histogram, a block of the region of interest is selected from among the plural blocks using a region-of-interest position determination condition that defined a condition to determine a region-of-interest position in the X-ray image with the image statistical information and image statistical information about the respective blocks, a feedback value to be used for controlling a brightness value of the region of interest is calculated based on a brightness value of the block selected as the region of interest, and X-ray irradiation conditions are determined so that the feedback value is a predetermined target brightness value.

Advantageous Effects of Invention

According to the present invention, ABS control can be performed by tracking object position movement to calculate a feedback value without performing setting operation for a region of interest by an operator, which can reduce an operator's load.

BRIEF DESCRIPTION OF DRAWINGS

FIG. 1 is a block diagram showing a configuration of an X-ray image diagnostic apparatus related to the present embodiment.

FIG. 2 is a functional block diagram of an X-ray image diagnostic apparatus related to the present embodiment.

FIG. 3 is a flow chart showing a process flow of an X-ray image diagnostic apparatus related to the first embodiment.

FIG. 5 is an explanatory diagram showing information about a region-of-interest position determination condition in which a procedure is associated with a region-of-interest position determination condition.

FIG. 6 is an explanatory diagram showing a fluoroscopic image and a histogram generated based on the fluoroscopic image, (a) shows an example of the fluoroscopic image, and (b) shows a histogram of the fluoroscopic image.

FIG. 9 is an explanatory diagram showing a conversion process from a feedback brightness value into irradiation conditions.

DESCRIPTION OF EMBODIMENTS

Figure 4:
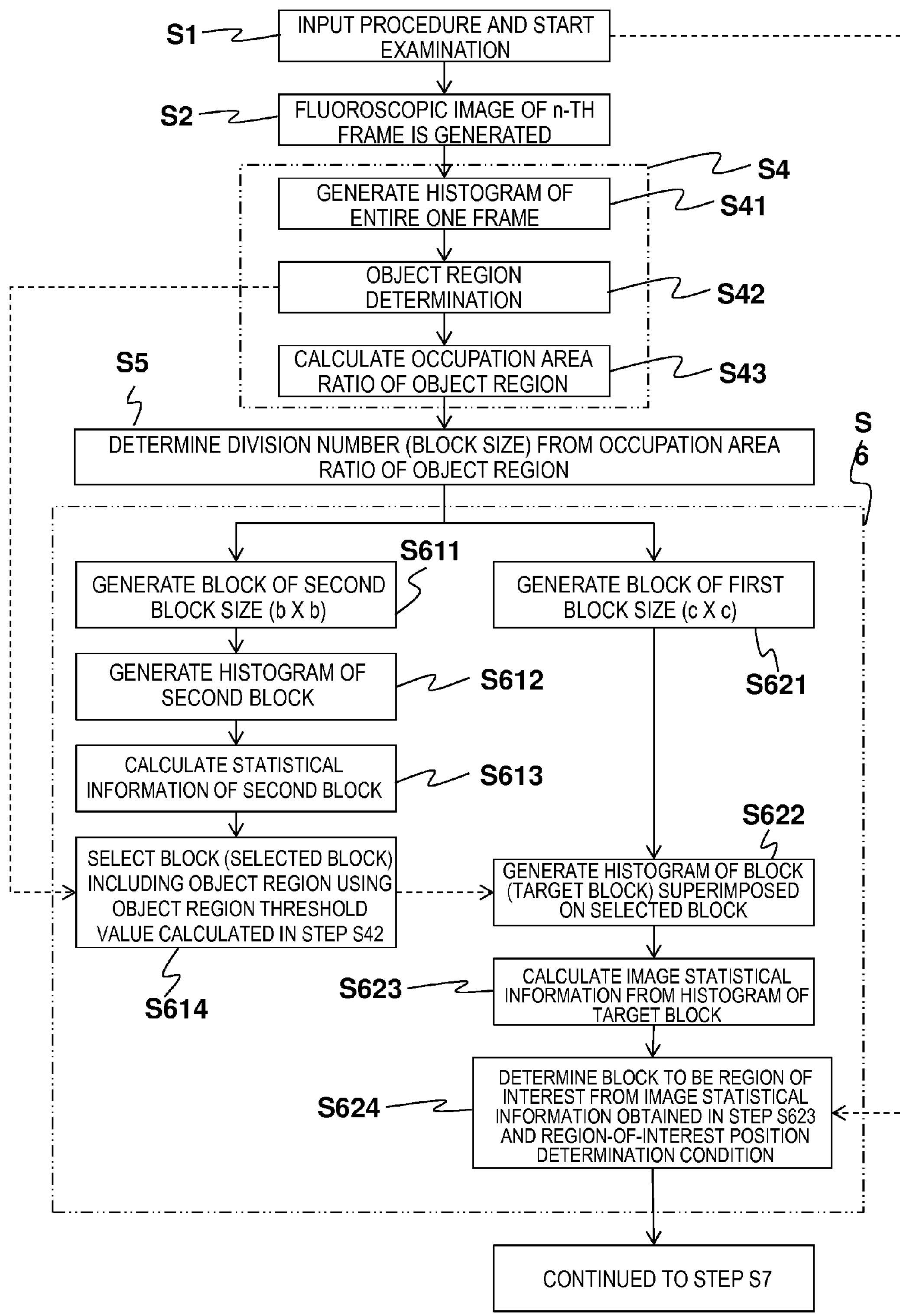
FIG. 4 is a flow chart showing a process flow of ABS control.

An X-ray image diagnostic apparatus related to the present embodiment includes an X-ray generating device generating an X-ray, an X-ray detector detecting the X-ray transmitted through an object and outputting a transmission X-ray signal, an image generating unit generating an x-ray image of the object based on the transmission X-ray signal, a block generating unit generating a plurality of blocks by dividing the x-ray image into a plurality of regions, a histogram generating unit generating a histogram showing distribution of brightness values for each of the plural blocks, a region-of-interest position selection unit selecting a block of a region of interest from among the plural blocks using a predetermined region-of-interest position determination condition and a histogram of the respective blocks, a feedback value calculation unit calculating a feedback value used for controlling a brightness value of the region of interest based on a brightness value of the block selected as the region of interest, an irradiation condition determining unit determining irradiation conditions of the X-ray so that the feedback value reaches a predetermined target brightness value, and an image display device displaying the X-ray image.

Also, the region-of-interest position selection unit in the above X-ray image diagnostic apparatus uses image statistical information calculated based on a histogram of the respective blocks to select a block of a region of interest from among the plural blocks.

Also, the above X-ray image diagnostic apparatus has a block statistical information calculation unit calculating the image statistical information.

Also, the image statistical information in the above X-ray image diagnostic apparatus is at least any one of an average brightness value, the number of histogram peaks, a brightness of a histogram peak, or a dispersion value.

Also, the above X-ray image diagnostic apparatus has a determination condition storage unit storing the region-of-interest position determination condition.

Also, the above X-ray image diagnostic apparatus further includes a procedure selecting unit selecting an examination procedure; the determination condition storage unit stores the region-of-interest position determination condition for the examination procedure; and the region-of-interest position selection unit extracting the region-of-interest position determination condition according to the selected procedure to select a block of the region of interest using the region-of-interest position determination condition.

Also, the above X-ray image diagnostic apparatus further includes an object region ratio calculation unit calculating a ratio occupied by an object region that is comprised of regions where the object is imaged in the X-ray image, and the block generating unit determines a division number used for dividing the X-ray image into a plurality of regions according to the rate occupied by the object region.

Also, the above X-ray image diagnostic apparatus further includes an object block selection unit selecting a block that includes the object region, the block generating unit determines at least two different division numbers according to the ratio occupied by the object region and generates first blocks divided by a relatively large division number and second blocks divided by a relatively small division number, the object block selection unit selects a block that includes the object region from among the second blocks, and the histogram generating unit generates the histogram for the first blocks including at least a part of the selected second blocks.

Also, the above X-ray image diagnostic apparatus further includes an entire histogram generation unit generating a histogram of an entire X-ray image that the image generating unit generated and an object region detecting unit where a histogram generated by the entire histogram generation unit is divided into two data groups using an arbitrary brightness value as a border; a brightness value is considered to be an object region threshold value when a dispersion value between two classes of the respective data groups or an index value that increases and decreases in conjunction with the dispersion value between these classes is maximum; and a data group less than the object region threshold value is detected as an object region, and the object region ratio calculation unit calculates a ratio for which the detected object region accounts in the X-ray image.

Also, the block generating unit in the above X-ray image diagnostic apparatus selects a block that includes a brightness value less than the object region threshold value as a block that includes the object region.

Also, the above X-ray image diagnostic apparatus further includes an X-ray diaphragm that restricts an irradiation region of the X-ray, the entire histogram generation unit generates a histogram of a region inside a region where the X-ray diaphragm is imaged in the X-ray image, and the block generating unit divides the inside region into the plural regions.

Also, the feedback value in the above X-ray image diagnostic apparatus is an average brightness value or median of a block selected as the region of interest.

Also, the above X-ray image diagnostic apparatus further includes a metal region threshold storage unit specifying a metal region threshold to determine a region where metal is imaged for the examination procedure in the X-ray image, and the feedback value calculation unit sets the metal region threshold according to the selected procedure and calculates the feedback value using a brightness value of the set metal region threshold or more from among brightness values of blocks selected as the region of interest.

Also, a control method of an X-ray generating device related to the present embodiment includes a unit generating a plurality of blocks by dividing an X-ray image of an object into a plurality of regions, a unit generating a histogram showing distribution of brightness values for each of the plural blocks, a unit selecting a block of the region of interest from among the plural blocks using a predetermined region-of-interest position determination condition and a histogram of the respective blocks, a unit calculating a feedback value to be used for controlling a brightness value of the region of interest based on a brightness value of a block selected as the region of interest, and a unit determining irradiation conditions of the X-ray so that the feedback value reaches a predetermined target brightness value.

Hereinafter, embodiments of the present invention will be described more specifically using diagrams. Configurations having the same function and procedures of the same processing content are denoted by the same reference numerals, and the explanations thereof will not be repeated.

In the present embodiment, the X-ray image diagnostic apparatus 10 generating an X-ray image (hereinafter, referred to as "fluoroscopic image") comprised of dynamic images and an X-ray image comprised of static images will be described as an example. However, an X-ray image diagnostic apparatus imaging a static image may be that performing fluoroscopy only when brightness values of plural static images are adjusted. Hereinafter, the overview configuration of an X-ray image diagnostic apparatus related to the present embodiment will be described based on FIGS. 1 and 2. FIG. 1 is a block diagram showing a configuration of an X-ray image diagnostic apparatus related to the present embodiment. FIG. 2 is a functional block diagram of an X-ray image diagnostic apparatus related to the present embodiment.

As shown in FIG. 1, the X-ray image diagnostic apparatus 10 related to the present embodiment is comprised of the X-ray tube 1 generating an X-ray, the X-ray generator 2 applying a high voltage to the X-ray tube 1 according to an irradiation condition signal (for example, a signal showing a tube current and a tube voltage), the X-ray control device 3 transmitting a feedback voltage signal to determine irradiation conditions for the X-ray generator 2, the X-ray flat surface detector 4 being disposed facing the X-ray tube 1 and detecting an X-ray transmitted through an object, the X-ray flat surface detector control device 5 controlling a readout process etc. of the detected transmission X-ray signal, the image processing device 6 that generates a fluoroscopic image based on the read-out transmission X-ray signal; calculates a feedback brightness value based on the fluoroscopic image; outputs a feedback brightness value signal showing the brightness value to the X-ray control device 3; and then generates a fluoroscopic image for display, the image display device displaying a fluoroscopic image, the system control device performing control for the X-ray control device 3, the X-ray flat surface detector control device 5, and the image processing device 6, and the table 9 to place an object.

Additionally, in a position opposite to the X-ray flat surface detector 4 in the X-ray tube 1, the X-ray diaphragm 11 restricting an irradiation region of an X-ray is provided, and the system control device 8 obtains position information of the X-ray diaphragm 11 as well as controls the diaphragm amount. Additionally, the procedure selecting unit 12 selecting a procedure that specifies at least one of an imaging site and an examination type for the system control device 8 is provided, selection information from the procedure selecting unit 12 is input into the system control device 8, and then the selection information is transmitted from the system control device 8 to the image processing device 6. In the present embodiment, a condition to determine a region-of-interest position is selected for the above selected procedure, and the details will be described later. Also, the X-ray tube 1 and the X-ray generator 2 are collectively referred to as an X-ray generating device.

As shown in FIG. 2, the image processing device 6 mainly includes the image generation unit 60 generating a fluoroscopic image based on a transmission X-ray signal output from the X-ray flat surface detector 4, the ABS control processing unit 61 calculating an ABS feedback value, and the display image processing unit 62 performing image display processing based on a fluoroscopic image generated from the image generation unit 60.

The image generation unit 60 generates an image in frame units based on a transmission X-ray signal output from the X-ray flat surface detector 4.

The ABS control processing unit 61 is comprised of the entire histogram generation unit 6*a* generating a histogram that shows distribution of brightness values in a one-frame image, the object region detecting unit 6*b* detecting a region where an object included in each frame is imaged (hereinafter, referred to as "object region") based on the histogram, the object region ratio calculation unit 6*c* calculating a ratio that a detected object region accounts for in the entire one frame, and the block generation unit 6*d* determining a division number according to an object ratio and generating divided images where one frame is divided into a plurality of regions by the division number.

Hereinafter, the respective divided images are referred to as "block". In the present embodiment, the block generation unit 6*d* has the first block that was divided by a relatively large number and the second block that was divided by a relatively small number. Sizes of the first block and the second block are referred to as the first block size and the second block size respectively. The first block size is comprised of image sizes smaller than the second block size.

Additionally, the ABS control processing unit 61 is comprised of the first block histogram generation unit 6*e* generating a histogram that shows distribution of brightness values of the first block, the first block statistical information calculation unit 6*f* calculating statistical information to be used for selecting a region-of-interest position for each histogram of the first block, the region-of-interest position selection unit 6*g* selecting a region-of-interest position from among the first block by comparing the above statistical information with a region-of-interest position determination condition determined according to a procedure selected in the procedure selecting unit 12, the feedback value calculation unit 6*h* calculating an ABS feedback brightness value using a brightness value in a region of interest selected in the region-of-interest position selection unit 6*g*, and the determination condition storage unit 6*i* storing region-of-interest position determination condition information that shows a region-of-interest position determination condition for each procedure.

Additionally, the ABS control processing unit 61 is comprised of the second block histogram generation unit 6*j* generating a histogram that shows distribution of brightness values of the second block, the second block statistical information calculation unit 6*k* calculating statistical information to determine whether an object region is included for each histogram of the second block, and the object block selection unit 6*l* selecting the second block including an object region based on the above statistical information as preparation before determining the first block.

The first block histogram generation unit 6*e* generates a histogram of the first block that is different from the position of or that includes a part of the second block selected in the object block selection unit 6*l*. Also, although the second block histogram generation unit 6*j*, the second block statistical information calculation unit 6*k*, and the object block selection unit 6*l* are not a required configuration to reduce the number of the first block that is a target for generating a histogram in the first block histogram generation unit 6*e*, the first embodiment to be described below is to include the second block histogram generation unit 6*j*, the second block statistical information calculation unit 6*k*, and the object block selection unit 6*l*.

On the other hand, the display image processing unit 62 performs image processing to generate a display fluoroscopic image such as display gradation processing for a transmission X-ray signal read out from the X-ray flat surface detector 4, and then outputs and displays the display fluoroscopic image on the image display device 7.

The X-ray control device 3 includes the feedback voltage calculation unit 3*a* that converts a feedback brightness value received from the feedback value calculation unit 6*h* of the image processing device 6 into a voltage (hereinafter, referred to as "feedback voltage").

Also, the X-ray generator 2 includes the irradiation condition determining unit 2*a* to determine irradiation conditions (tube current/tube voltage) so that a feedback voltage received from the X-ray control device 3 corresponds to the standard voltage where a brightness value (hereinafter, referred to as "target brightness value") desired by a region of interest in a fluoroscopic image is converted into a voltage.

The image generation unit 60, the respective components in the ABS control processing unit 61, and the display image processing unit 62 may be configured so that a program which achieves the above respective functions is incorporated in a hardware device which executes the program, for example.

First Embodiment

Figure 7:
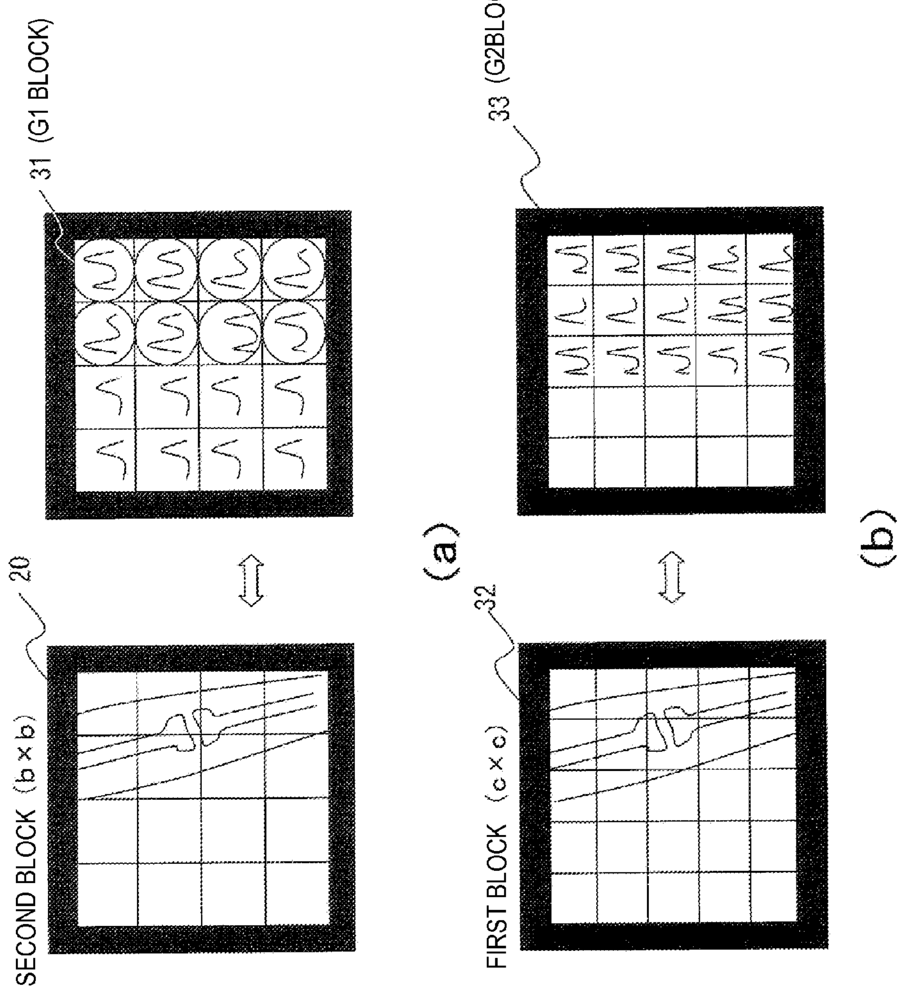
FIG. 7 is an explanatory diagram showing a selected block and a target block as well as those histograms, (a) shows a selected block selected based on a block of the first block size and a histogram of the respective blocks, and (b) shows a block of the second block size and a histogram of target blocks.
Figure 8:
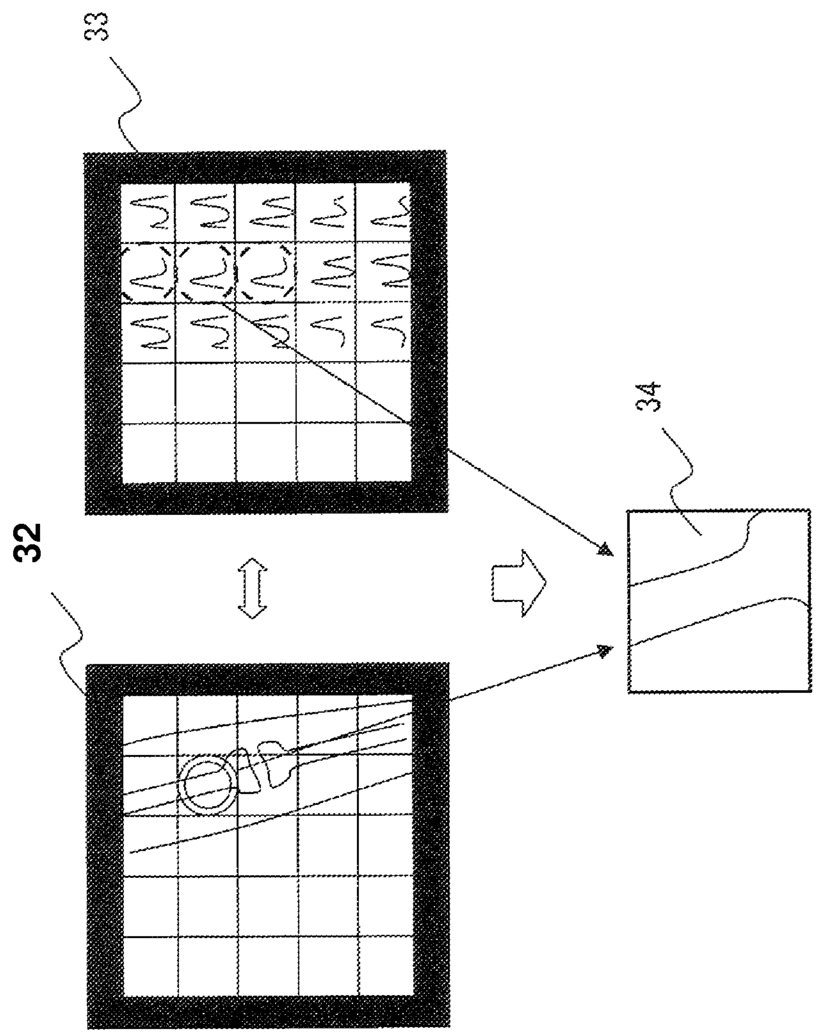
FIG. 8 is an explanatory diagram showing a process to select a region of interest from among target blocks.

The first embodiment will be described based on FIGS. 3 to 8. FIG. 3 is a flow chart showing a process flow of an X-ray image diagnostic apparatus related to the first embodiment. FIG. 4 is a flow chart showing a process flow of ABS control. FIG. 5 is an explanatory diagram showing information about a region-of-interest position determination condition in which a procedure is associated with a region-of-interest determination condition. FIG. 6 is an explanatory diagram showing a fluoroscopic image and a histogram generated based on the fluoroscopic image, (a) shows an example of the fluoroscopic image, and (b) shows a histogram of the fluoroscopic image. FIG. 7 is an explanatory diagram showing a selected block and a target block as well as those histograms, (a) shows a selected block selected based on a block of the first block size and a histogram of the respective blocks, and (b) shows a block of the second block size and a histogram of target blocks. FIG. 8 is an explanatory diagram showing a process to select a region of interest from among target blocks. FIG. 9 is an explanatory diagram showing a conversion process from a feedback brightness value into irradiation conditions.

First, based on FIGS. 3 and 4, the process flow of the X-ray image diagnostic apparatus 10 related to the first embodiment will be described. The process flow for displaying a fluoroscopic image from Step S2 to Step S3 is performed parallel with that for ABS control from Steps S2 and S4 to S9 by the X-ray image diagnostic apparatus 10. Hereinafter, the explanation will be sequentially made along the steps in FIGS. 3 and 4.

(Step S1)

An operator determines an examination procedure to be performed later, selects and inputs the procedure in the procedure selecting unit 12, and then starts the examination (fluoroscopy) (S1). In the procedure to be determined here, information such as an imaging site (for example, an arm, a lower extremity, the chest, etc.) and an examination procedure etc. (fluoroscopy and imaging) is included. The system control device 8 transmits information showing a procedure selected for the region-of-interest position selection unit 6*g*.

Region-of-interest position determination condition information where a procedure corresponds to a region-of-interest position determination condition is stored in the determination condition storage unit 6*i* in advance. A region-of-interest position determination condition is that specifying a condition to determine a region-of-interest position in an X-ray image and is set using image statistical information calculated based on a histogram in an X-ray image or the histogram. Also, image statistical information is a region-of-interest position determination parameter that is at least one of or a combination of an average brightness value, the number of histogram peaks, brightness values of histogram peaks, and a dispersion value, a region-of-interest position determination condition is determined using the region-of-interest position determination parameter. Also, a different region-of-interest position determination parameter may be used depending on the procedure. For example, in order to focus on bones in the procedure 1 "orthopedics/arm" case, the following region-of-interest position determination conditions are specified using two region-of-interest position determination parameters of the number of histogram peaks and an average brightness value in region-of-interest position determination condition information of FIG. 5.

Condition 1: blocks of which the number of histogram peaks is 1

Condition 2: a block of which an average brightness value in the block is the smallest among the blocks meeting Condition 1

The region-of-interest position determination conditions vary depending on the procedure, and the following two conditions are specified in "Procedure 2" to focus on organs for example.

Condition 1': blocks of which the number of histogram peaks is 1

Condition 2': a block of which a dispersion value of a brightness value in the block is the smallest among the blocks meeting Condition 1'

Region-of-interest position determination condition information of FIG. 5 is just an example. For example, region-of-interest position determination conditions may be determined with three or more conditions included.

The region-of-interest position selection unit 6*g* performs a search in the determination condition storage unit 61*i* to retrieve region-of-interest position determination condition information corresponding to a selected procedure. The information will be used in Step S624 (see FIG. 4) to be described later.

(Step S2)

A transmission X-ray signal of the n-th frame from X-ray flat surface detector 4 is input to the image generation unit 60 to generate a fluoroscopic image of the n-th frame (S2). For example, as shown in FIG. 6, it is supposed that the fluoroscopic image 20 in one frame comprised of fluoroscopic images of an arm in an orthopedic procedure is input.

(Step S3)

The display image processing unit 62 performs image display processing such as display gradation processing for an input fluoroscopic image, generates a fluoroscopic image for display, and then displays it on the image display device 7 (S3). The procedure proceeds to Step S9.

(Step S4)

An object region ratio of an entire fluoroscopic image in one frame is calculated (S4).

(Step S41)

The entire histogram generation unit 6*a* generates a histogram showing distribution of brightness values (or pixel values) for the entire fluoroscopic image 20 (see (a) in FIG. 6) of one frame input in Step S2 (S41). In the present embodiment, it is supposed that the histogram 23 shown in (b) in FIG. 6 is generated. Also, in order to process the following Step S42 at a higher speed, a compressed histogram in which an N-bit histogram is thinned out a few bit at a time is generated, and then processes of Steps S42 and S43 may be performed using the compressed histogram.

(Step S42)

The object region detecting unit 6*b* uses the histogram 23 of the entire one frame generated in Step S41 to calculate a brightness value $PV_{threshold}$ that is a threshold value between an object region and a halation region (S42). In the present embodiment, a brightness value $PV_{threshold}$ is referred to as an object region threshold value that is calculated using the discriminant analysis method.

The object region detecting unit 6*b* uses an arbitrary brightness value on the histogram 23 as a boundary to divide the histogram into two, and then calculates a brightness value of which the dispersion between classes is the maximum when the divided histograms are presumed as Class 1 and Class 2 respectively as a brightness value $PV_{threshold}$. Specifically, a value of the dispersion between classes Δ is calculated by the following formula (1), and then a brightness value $PV_{threshold}$ for when the Δ value is the maximum is calculated.

$$\Delta=\{\omega_1(\mu_1-\mu_a)^2+\omega_2(\mu_2-\mu_a)^2\}/(\omega_1+\omega_2) \quad (1)$$

Δ: value of dispersion between classes $\omega_1$: ratio of the number of pixels of Class 1

$\omega_2$: ratio of the number of pixels of Class 2

$\mu_1$: average brightness value of Class 1

$\mu_2$: average brightness value of Class 2

$\mu_a$: average brightness value of an entire image

Also, the denominator $(\omega_1+\omega_2)$ on the right side of the formula (1) shows all the number of pixels of a fluoroscopic image in one frame, and the value is the same for all the frames comprising the fluoroscopic image. Therefore, omitting the calculation divided by $(\omega_1+\omega_2)$ on the right side of the formula (1), a brightness value $PV_{threshold}$ dispersion for when the between classes A is the maximum may be calculated using the following formula (1)'. The following formula (1)' is a formula to calculate an index value Δ' fluctuating with dispersion between classes, and the dispersion between classes Δ is the maximum when Δ' is the maximum. By using the formula (1)' instead of the formula (1), the calculation divided by $(\omega_1+\omega_2)$ can be omitted, which can perform higher calculation processing.

$$\Delta'=\omega_1(\mu_1-\mu_a)^2+\omega_2(\mu_2-\mu_a)^2 \quad (1)'$$

Δ': index value fluctuating with a value of dispersion between classes $\omega_1$: ratio of the number of pixels of Class 1

$\omega_2$: ratio of the number of pixels of Class 2

$\mu_1$: average brightness value of Class 1

$\mu_2$: average brightness value of Class 2

$\mu_a$: average brightness value of an entire image

The fluoroscopic image 20 in FIG. 6(*a*) is comprised of the direct line region 21 where an X-ray directly enters into the x-ray flat surface detector 4 and the object region 22 where an X-ray transmitted through an object enters. The histogram 23 of the fluoroscopic image 20, as shown in FIG. 6(*b*), is diphase and comprised of a region where high brightness values of pixels comprising the direct line region 21 mainly are distributed and a region where brightness values of pixels comprising the object region 22 are distributed. In this case, a brightness value $PV_{threshold}$ (24 in FIG. 6) where the dispersion between classes is the maximum is to be a trough between two peaks. Therefore, a data group of brightness values that are $PV_{threshold}$ (24 in FIG. 6) or more and a data group (Target PS) of brightness values less than $PV_{threshold}$ can be recognized as the direct line region 25 and the object region 26 respectively.

(Step S43)

The object region ratio calculation unit 6*c* calculates an exclusive area ratio P in one frame in an object region calculated in Step S42 (S43). An exclusive area ratio P is calculated as a ratio of the number of pixels in the object region 26 to all the number of pixels of the histogram 23 based on the following formula (2).

$$P(\%)=C_{sp}\div C_{all} \quad (2)$$

P: ratio of the object region 26 calculated to the whole of the histogram 23

$C_{sp}$: the number of pixels of the object region 26 in the histogram 23

$C_{all}$: the number of pixels of the entire histogram 23

(Step S5)

Based on an exclusive area ratio P of an object region, a division number to divide a fluoroscopic image of one frame into a plurality of regions is determined (S5).

In the present embodiment, the block generation unit 6*d* determines at least two division numbers from among plural types of division numbers prepared in advance based on an exclusive area ratio P of an object region calculated in Step S5.

Preparing three types (a×a, b×b, c×c (a>b>c)) of division numbers in advance, two types from among them are determined for block generation. Of the two types of division numbers, the first block is that divided by a relatively larger division number, and the second block is that divided by a relatively smaller division number. Therefore, when a division number is determined, the block size is also determined.

The block generation unit 6*d* uses division numbers of a×a and b×b as shown in the following condition formula (3) when an exclusive area ratio P is $X_1$(%) set in advance or more (that is, when an object region is large). Conversely, when P is less than $X_1$(%), the division numbers of b×b and c×c are to be used.

$$\left.\begin{array}{l} P \geqq X_1 \rightarrow \text{division numbers of } a\times a \text{ and } b\times b \text{ are used} \\ P < X_1 \rightarrow \text{division numbers of } b\times b \text{ and } c\times c \text{ are used} \end{array}\right\} \quad (3)$$

For example, if the fluoroscopic image 20 of FIG. 6 is $P(\%)<X_1(\%)$, the first block size is a block size divided by c×c, and the second block size is a block size divided by b×b.

(Step S6)

Image statistical information is calculated based on a block histogram in order to select a region-of-interest position (S6).

(Step S611)

The block generation unit 6*d* uses the second block size from among at least two types of division numbers determined in Step S5 to generate a block (S611). In the above example, a block size divided by b×b is used.

(Step S612)

The second block histogram generation unit 6*j* generates a histogram showing distribution of brightness values for the respective blocks of the second block size (S612). In the above example, the second block histogram generation unit 6*j*, as shown in FIG. 7(*a*), the fluoroscopic image 20 is divided into b×b in order to generate the histogram 31 of each block.

(Step S613)

The second block statistical information calculation unit 6*k* calculates image statistical information in each block based on each histogram generated in Step S612 (S613). In the present embodiment, although brightness values in a block are calculated, image statistical information to be used for determining whether there is an object region or not may be calculated.

As an example of statistical information, there is a method to perform "threshold value determination by a dispersion value" for each divided block. For example, a pixel value in the block is to apply to any of the following three cases.

(1) In a case where all the pixels in the block are direct line (halation) regions: because brightness values of pixels in a block shows almost same values, a dispersion value becomes relatively small.

(2) On the other hand, in a case where both of a direct line and an object region are included in pixels in a block: because brightness value distribution becomes large in a block, a dispersion value becomes relatively large.

(3) Also, in a case where pixels in a block are in an object region: because an object is comprised of various parts (bones, muscles, skins, etc.), a dispersion value becomes relatively large.

The sizes of the dispersion values in the above three cases are shown in the order of (2)>(3)>(1). Therefore, a threshold value is provided between (3) and (1) to perform threshold value determination, which can determine whether a block includes an object region or not.

The object block selection unit 6*l* compares an object region threshold value $PV_{threshold}$ calculated in Step S42 with a brightness value in each block calculated in S613 to select the second block including an object region (S614). Hereinafter, a block selected here is referred to as the selected block G1.

In the present embodiment, the selection condition is that pixels of a brightness value less than an object region threshold value $PV_{threshold}$ are included at least more than one pixel in each block. From among the respective histograms 31 in FIG. 7(*a*), the circled blocks are the selected blocks G1.

(Step S621)

The block generation unit 6*d* generates the first block using a relatively large division number determined in Step S5 (S621). The present embodiment generates a block divided into c×c (see the block 32 in FIG. 7(*b*)). Also, although the present step is described subsequently to Step S614 for convenience of description, the present step may be performed parallel to the already-described Step S611 after two kinds of division numbers are determined in Step S5.

(Step S622)

The first block histogram generation unit 6*e* generates a histogram only for a block that is superimposes on or corresponds to the selected block G1 among the first blocks. Hereinafter, a block that is superimposes on or corresponds to the selected block G1 among the first blocks is referred to as "the selected block G2".

In FIG. 7(*b*), a block where the histogram 33 is described is the target block G2.

(Step S623)

The first block statistical information calculation unit 6*f* calculates statistical information to be used for region-of-interest position selection using the histogram 33 of the target block G2 (S623). The statistical information to be calculated includes, for example, an average brightness value, the number of histogram peaks, a histogram peak brightness value, a dispersion value of pixels in a block, etc.

Also, the first block statistical information calculation unit 6*f* obtains region-of-interest position determination conditions retrieved in Step S1, and only statistical information used for a region-of-interest position determination parameter which is being used for the region-of-interest position determination conditions may be calculated.

(Step S624)

The statistical information obtained in Step S623 and the region-of-interest position determination conditions searched in Step S1 are used for selecting a block serving as a region of interest from among the target blocks G2 (S624).

In the histogram 33 of FIG. 8, the blocks circled with a dashed line is the target block G2 that meets the condition 1, and the double-circled block in the image 32 of FIG. 8 is the target block G2 that meets the condition 2. Therefore, the double-circled block 34 is selected as a region of interest.

(Step S7)

A feedback brightness value $PV_{ABS}$ is calculated based on a brightness value in a region of interest (S7). In the present embodiment, the feedback value calculation unit 6*h* calculates an average brightness value of the block 34 serving as a region of interest selected in Step S6, and the average brightness value is used as a feedback brightness value $PV_{ABS}$. The feedback value calculation unit 6*h* transmits a signal (hereinafter, referred to as "feedback value signal") showing a feedback brightness value $PV_{ABS}$ to the x-ray control device 3. A median may be used as a representative of a brightness value in a region of interest instead of an average brightness value.

(Step S8)

Irradiation conditions are determined so that a feedback brightness value $PV_{ABS}$ is converted into a feedback voltage so as to corresponds to a brightness value (hereinafter, referred to as "target brightness value") to be kept more stable by ABS control processing (S8).

The feedback voltage calculation unit 3*a* in the x-ray control device 3 receives a feedback brightness value signal from the feedback value calculation unit 6*h*. Then, the feedback voltage calculation unit 3*a* converts a received feedback brightness value into a voltage (hereinafter, referred to as "feedback voltage") feeding back to the X-ray generator 2. The irradiation condition determining unit 2*a* of the X-ray generator 2 compares a feedback voltage with a predetermined standard voltage (voltage corresponding to a target brightness value) and gradually raises current irradiation conditions (a combination of a tube voltage and a tube current) if the feedback voltage is lower than the standard voltage to adjust the voltage so as to correspond to the standard voltage (for example, 5 V). Conversely, if the feedback voltage is higher than the standard voltage, the current irradiation conditions (a combination of a tube voltage and a tube current) are gradually lowered to adjust the voltage so as to correspond to the standard voltage (for example, 5 V).

Based on FIG. 9, conversion from a feedback brightness value into an irradiation condition will be described. In FIG. 9, it is determined that appropriate brightness adjustment is being performed when a feedback voltage is the same as a standard voltage $Y_{ref}$[V].

In FIG. 9, $PV_{ABS}=X_1$ is calculated by the feedback value calculation unit 6*h* from the current fluoroscopic image (n-th frame), and then, based on this, the feedback voltage calculation unit 3*a* converts a feedback brightness value $X_1$ into a feedback voltage $Y_1$[V]. The irradiation condition determining unit 2*a* compares a standard voltage $Y_{ref}$[V] with a feedback voltage $Y_1$[V], and if $Y_1$[V] is smaller compared with a standard voltage $Y_{ref}$[V], the current irradiation conditions ($mA_1$, $kV_1$) are raised to ($mA_2$, $kV_2$) (in case of $mA_1<mA_2$, $kV_1<kV_2$). Then, a fluoroscopic image of the n+1-th frame is imaged under a new irradiation condition: (mA, kV)=($mA_2$, $kV_2$). A feedback brightness value $PV_{ABS}=X_2$ calculated based on the n+1-th frame is to be $Y_2$[V] by converting into a feedback voltage. Because a feedback voltage and a standard voltage correspond with each other when a value of $Y_2$[V] is the same as that of $Y_{ref}$[V] ($Y_2$[V]=$Y_{ref}$[V]), the irradiation condition determining unit 2*a* determines that there is no need to change irradiation conditions. Therefore, the n+2-th frame is imaged under the condition: (mA, kV)=($mA_2$, $kV_2$).

In the present embodiment, although irradiation conditions are described using a combination of a tube current and a tube voltage, the irradiation conditions may be changed by raising and lowering only a tube current or a tube voltage.

(Step S9)

After changing irradiation conditions, a fluoroscopic image of the n+1-th frame is imaged (S9). The X-ray generator 2 outputs a newly determined irradiation condition signal to the X-ray tube 1, and then imaging a fluoroscopic image of the n+1-th frame is performed according to the new irradiation conditions. Then, going back to Step S2, a transmission X-ray signal of the n+1-th frame is input to the image processing device 6, and the subsequent processes after Step S2 are performed again based on the transmission X-ray signal.

According to the present embodiment, without performing setting operation for a region of interest by an operator, ABS control can be performed by tracking movement of an object position to calculate a feedback value, which can save the effort of the operator.

Additionally, by using conditions according to the procedure when a region of interest is determined, a brightness value of a site of interest that changes according to the procedure can be kept stable among frames and be displayed.

Also, a plurality of block sizes are used, a selected block including an object region is retrieved using the second block size of a relatively large size, only a block of the first block size that is superimposed on the selected block is selected as a target block, and statistical information to detect a region-of-interest position is calculated only for the target block, which can expect to achieve a higher processing speed compared to when the statistical information to detect the region-of-interest position is calculated for all the blocks of the first block size.

Second Embodiment

Figure 10:
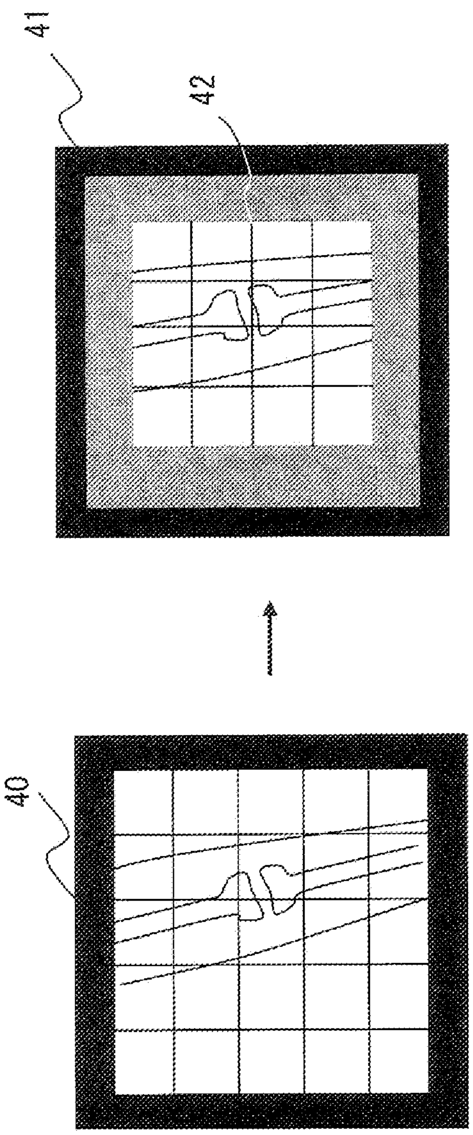
FIG. 10 is an explanatory diagram showing processing contents of the second embodiment.

In addition to the first embodiment, the second embodiment is an embodiment that excludes pixels in which a brightness value of an X-ray diaphragm is reflected from the target for ABS control processing. When the X-ray diaphragm 11 is inserted or when a fluoroscopic image is enlarged while a fluoroscopic image is being obtained, a position where the X-ray diaphragm 11 is inserted is detected automatically, and then object region determination and block generation are performed using only pixels inside the X-ray diaphragm 11. Hereinafter, the second embodiment will be described based on FIG. 10. FIG. 10 is an explanatory diagram showing processing contents of the second embodiment. Also, the process flow is similar to the first embodiment and will be described using the step numbers in FIGS. 3 and 4 again.

The fluoroscopic image 40 in FIG. 10 shows a state where a fluoroscopic image is divided into c×c (5×5 in FIG. 10) in Step S611 in case without the X-ray diaphragm 11. The fluoroscopic image 41 in FIG. 10 is a fluoroscopic image in which the X-ray diaphragm 11 is inserted and shows a state where the fluoroscopic image is divided into b×b (4×4 in FIG. 10) in Step S611. Position information of the X-ray diaphragm 11 is obtained when the system control device 8 controls operation of the X-ray diaphragm 11. Therefore, by outputting the position information from the system control device 8 to the image processing device 6, the X-ray diaphragm 11 can detect the region 42 imaged in a fluoroscopic image.

This detection is performed by the object region detecting unit 6*b* in Step S42 to perform object region determination for a fluoroscopic image that is on a side inner than the region 42. Then, in the object region ratio calculation process in Step S43, an exclusive area ratio P of an object region to an image that is on a side inner than the region 42 is calculated. In Step S5, a division number (or a block size) is determined based on the exclusive area ratio, and in Steps S611 and S621, an image that is on a side inner than the region 42 is divided using the division number (block size) determined above. As shown also in FIG. 10, because the fluoroscopic image 41 in which the X-ray diaphragm 11 is inserted has a large exclusive area ratio of an object in an image compared to the fluoroscopic image 40 without a diaphragm, a division number determined in Step S5 is determined so that the size of one block is relatively large.

According to the present embodiment, if an X-ray diaphragm is imaged in a fluoroscopic image, pixels in which the brightness value is reflected can be excluded from a calculation target for ABS control processing, which can perform more appropriate ABS feedback without being influenced by the X-ray diaphragm.

Third Embodiment

Figure 11:
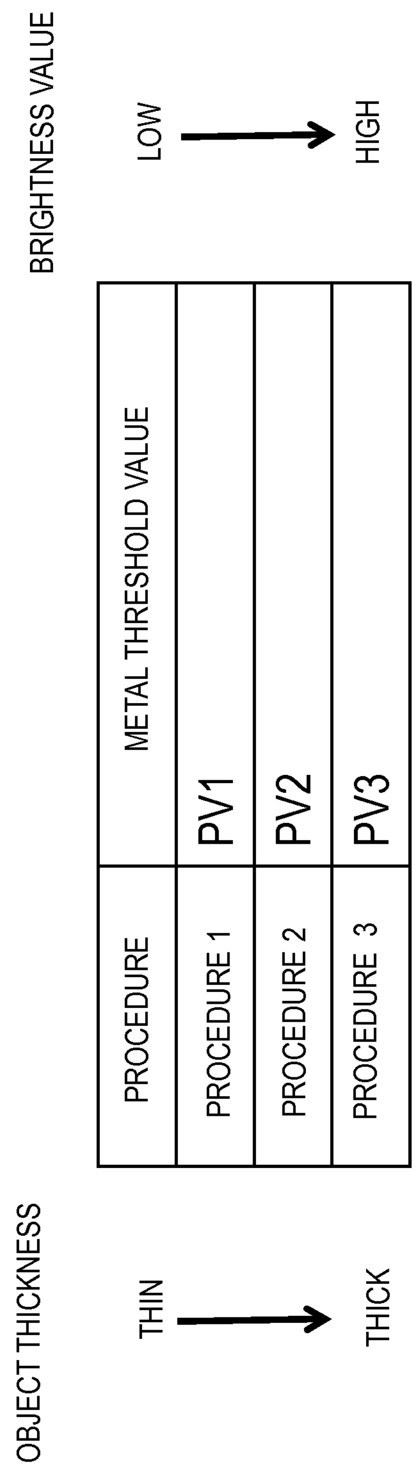
FIG. 11 is an explanatory diagram showing processing contents of the third embodiment.

In addition to the first embodiment, the third embodiment is an embodiment that excludes pixels, in which a brightness value of a region where metal is imaged is reflected, from the target for ABS control processing. Hereinafter, the third embodiment will be described based on FIG. 11. FIG. 11 is an explanatory diagram showing processing contents of the third embodiment.

The process flow is similar to the first embodiment and will be described using the step numbers in FIGS. 3 and 4 again.

Although one type of a metal region threshold value may be used, metal region threshold values that are comprised of arbitrary brightness values which are different for each procedure may also be used. For example, data of metal region threshold values that specifies a metal region threshold value corresponding to a procedure is stored in a storage unit in the image processing device 6 in advance. When a procedure is selected in Step S1, the feedback value calculation unit 6*h* may refer to metal region threshold value data to retrieve and set a metal region threshold value corresponding to a selected procedure. Then, in Step S624, if a pixel less than a brightness value of a preset metal region threshold value is included in a block selected as a region of interest, the pixel is excluded from calculation-target pixels of a feedback brightness value $PV_{ABS}$ to be calculated in Step S7.

An example of metal region threshold value data is shown in FIG. 11. In data of metal region threshold values in FIG. 11, as an object thickness gets thicker in the order of the procedure 1, procedure 2, and procedure 3, the metal region threshold values are defined using higher brightness values such as PV1, PV2, and PV3. Hence, a metal region threshold value can be used according to the procedure. For example, in a case where the procedure is an orthopedic one; the imaging site is an arm, an object thickness is thin, and an X-ray amount is also relatively small. Therefore, because metal in an image is imaged in a relatively dark manner, a relatively dark brightness value is set for a procedure including a site with a thin object thickness as a metal region threshold value. On the other hand, in a case where the procedure is thoracotomy; the imaging site is the chest, metal surgical instruments such as a thoracotomy fixture are imaged in an image. An object thickness of the chest is relatively thicker compared to that of the extremities, which results in relatively high doses of X-rays. Consequently, because metal surgical instruments are imaged in a relatively bright manner, a relatively bright brightness value is set for a procedure including a site with a thick object thickness as a metal region threshold value.

According to the present embodiment, when metal is imaged during fluoroscopy, pixels in which a brightness value of metal is reflected can be excluded from a calculation target for a feedback brightness value $PV_{ABS}$, which can reduce influence of a metal region for ABS control processing. Also, because an X-ray dose varies depending on the object thickness before an imaging brightness of metal varies according to this, a brightness value of metal can be excluded from a calculation target for a feedback brightness value $PV_{ABS}$ by using a metal region threshold value according to the object thickness.

Fourth Embodiment

The fourth embodiment is an embodiment to change the number of types of division numbers according to the fluoroscopic image size of one frame. Although two division numbers are determined in the first embodiment, if an object region is relatively small, only one type of the division number to generate the first block is determined, histograms are generated for all the first blocks, and then the statistic to select a region-of-interest position may be calculated. The process flow of the fourth embodiment overlaps partly with the first embodiment and will be described using the step numbers in FIGS. 3 and 4 again.

In the fourth embodiment, the object region detecting unit 6*b* is Step S43 calculates a total value of frequency of histograms generated in Step S41. If the total value is a predetermined first standard value or less, an image size of a fluoroscopic image can be determined to be relatively small. Therefore, the object region detecting unit 6*b* brings over comparison results between the total value and the first standard value to the block generation unit 6*d*, the block generation unit 6*d* determines only a division number to generate the first block based on the comparison results in a case where the total value is the first standard value or less. Consequently, the steps from Step S611 to Step S614 are omitted. In Step S622, histograms are generated for all the first blocks, and then the process of Step S623 is performed based on all the histograms.

An image size may be determined from the histogram frequency of the entire image as described above, or alternatively, may be determined depending on how much the X-ray diaphragm 11 is imaged on a screen in the second embodiment. For example, if a setting value on a screen showing that $X_2$% or more is imaged for example is detected from position information of the X-ray diaphragm 11, it may be configured so that the block generation unit 6*d* determines only one division number based on the detection result.

On the other hand, when the above total value is greater than the second standard value, this can be determined that an image size is large.

In this case, three or more division numbers are determined to generate blocks in order from the least division number, and then a block including an object region among the blocks is to be a selected block. This process is repeated until a block of a division number which is one more than that of the maximum number. Then, a selected block is to be a block where a block of a division number of the maximum number and a selected block that is selected using the division number of the maximum number are superimposed or partly included.

According to the present embodiment, when an image size is small, a target block can be directly retrieved without retrieving a selected block, and when an image size is large, a selected block can be retrieved through the plural steps.

DESCRIPTION OF REFERENCE NUMERALS

1: X-ray tube, 2: X-ray generator, 3: X-ray control device, 4: X-ray flat surface detector, 5: X-ray flat surface detector control device, 6: image processing device, 7: image display device, 8: system control device, 9: table, 10: X-ray image diagnostic apparatus, 11: X-ray diaphragm

The invention claimed is:

1. An X-ray image diagnostic apparatus comprising:

an X-ray generating device generating an X-ray;

an X-ray detector detecting the X-ray transmitted through an object and outputting a transmission X-ray signal;

an image generation unit generating an X-ray image of the object based on the transmission X-ray signal;

a block generation unit generating plural blocks by dividing the X-ray image into plural regions; and a histogram generation unit generating a histogram showing distribution of brightness values for each of the plural blocks, a region-of-interest position selection unit selecting a block serving as a region of interest from among the plural blocks using predetermined region-of-interest position determination conditions and histograms of the respective blocks;

a feedback value calculation unit calculating a feedback value used for controlling a brightness value of the region of interest based on a brightness value of a block selected as the region of interest;

an irradiation condition determining unit determining irradiation conditions of the X-ray so that the feedback value reaches a predetermined target brightness value; and an image display device displaying the X-ray image.

2. The X-ray image diagnostic apparatus according to claim 1, wherein the region-of-interest position selection unit selects a block serving as a region of interest from among the plural blocks using image statistical information calculated based on histograms of the respective blocks.

3. The X-ray image diagnostic apparatus according to claim 2, having:

a block statistical information calculation unit calculating the image statistical information.

4. The X-ray image diagnostic apparatus according to claim 3, wherein the image statistical information is at least any one of an average brightness value, the number of histogram peaks, a brightness of a histogram peak, and a dispersion value.

5. The X-ray image diagnostic apparatus according to claim 1, having:

a determination condition storage unit storing the region-of-interest position determination conditions.

6. The X-ray image diagnostic apparatus according to claim 5, further comprising:

a procedure selecting unit selecting an examination procedure, wherein the determination condition storage unit stores the region-of-interest position determination conditions corresponding to the examination procedure, the region-of-interest position selection unit provides the region-of-interest position determination conditions according to the selected procedure, and the region-of-interest position determination conditions are used for selecting a block that serves as the region of interest.

7. The X-ray image diagnostic apparatus according to claim 1, wherein for the X-ray image, an object region ratio calculation unit calculating a ratio of an object region that is comprised of regions where the object is imaged is further included, and the block generation unit determines a division number to be used for when the X-ray image is divided into plural regions according to a ratio of the object region.

8. The X-ray image diagnostic apparatus according to claim 7, further comprising:

an object block selection unit selecting a block that includes the object region, wherein the block generation unit determines at least two different division numbers according to a ratio of the object region and generates a first block divided by a relatively large division number and a second block divided by a relatively small division number, and the object block selection unit selects a block including the object region from among the second block, and the histogram generation unit generates the histogram for the first block including at least a part of the selected second block.

9. The X-ray image diagnostic apparatus according to claim 8, further comprising:

an entire histogram generation unit generating a histogram of an entire X-ray image that the image generation unit generates, and an object region detecting unit dividing a histogram that the entire histogram generation unit generates into two data groups at an arbitrary brightness value, taking a brightness value as an object region threshold value when an inter-class dispersion value of two classes comprised of the respective data groups or an index value that increases and decreases with the inter-class dispersion value reaches the maximum, and detecting a data group less than the object region threshold value as an object region, wherein the object region ratio calculation unit calculates a ratio of the detected object region to the X-ray image.

10. The X-ray image diagnostic apparatus according to claim 9, wherein the object block selection unit selects a block including a brightness value less than the object region threshold value as a block including the object region.

11. The X-ray image diagnostic apparatus according to claim 9, further comprising:

an X-ray diaphragm limiting an irradiation region of the X-ray, wherein the entire histogram generation unit generates a histogram of a region inner than that where the X-ray diaphragm was imaged in the X-ray image, and the block generation unit divides the inner region into the plural regions.

12. The X-ray image diagnostic apparatus according to claim 1, wherein the feedback value is an average brightness value of a block selected as a region of interest or the median.

13. The X-ray image diagnostic apparatus according to claim 6, further comprising:

a metal region threshold storage unit specifying a metal region threshold value to determine a region where metal is imaged in the X-ray image corresponding to the examination procedure, wherein the feedback value calculation unit sets the metal region threshold value according to the selected procedure and calculates the feedback value using a brightness value of the set metal region threshold value or more from among brightness values in a block selected as the region of interest.

14. A method for controlling an X-ray generation device including:

a plural-block generating step that generates plural blocks by dividing an X-ray image of an object into plural regions, a histogram generating step that shows distribution of brightness values for each of the plural blocks, a block selecting step that selects a block to serve as the region of interest from among the plural blocks using predetermined region-of-interest position determination conditions and histograms of the respective blocks, a feedback value calculating step that calculates a feedback value to be used for controlling a brightness value of the region of interest based on a brightness value of the block selected as the region of interest, and an X-ray irradiation condition determining step that determines irradiation conditions of the X-ray so that the feedback value reaches a predetermined target brightness value.

* * * * *